United States Patent
Georgeou et al.

(10) Patent No.: US 10,435,764 B2
(45) Date of Patent: Oct. 8, 2019

(54) METHOD FOR CALCULATING THE COMBINATION OF PROPERTIES BEING ESTABLISHED FOR A DEFORMABLE LIGHTWEIGHT STEEL

(71) Applicant: SALZGITTER FLACHSTAHL GMBH, Salzgitter (DE)

(72) Inventors: Zacharias Georgeou, Wolfsburg (DE); Frank Klose, Edemissen (DE)

(73) Assignee: Salzgitter Flachstahl GmbH, Salzgitter (DE)

( * ) Notice: Subject to any disclaimer, the term of this patent is extended or adjusted under 35 U.S.C. 154(b) by 399 days.

(21) Appl. No.: 15/304,743

(22) PCT Filed: Apr. 8, 2015

(86) PCT No.: PCT/DE2015/100147
§ 371 (c)(1),
(2) Date: Oct. 17, 2016

(87) PCT Pub. No.: WO2015/158328
PCT Pub. Date: Oct. 22, 2015

(65) Prior Publication Data
US 2017/0037490 A1 Feb. 9, 2017

(30) Foreign Application Priority Data

Apr. 17, 2014 (DE) ........................ 10 2014 005 662

(51) Int. Cl.
| | |
|---|---|
| *C21D 9/52* | (2006.01) |
| *B22D 11/06* | (2006.01) |
| *B21B 1/46* | (2006.01) |
| *C22C 38/02* | (2006.01) |
| *C22C 38/06* | (2006.01) |
| *C22C 38/38* | (2006.01) |
| *C21D 3/04* | (2006.01) |
| *C21D 8/02* | (2006.01) |
| *G01N 3/08* | (2006.01) |

(52) U.S. Cl.
CPC ............. *C21D 9/52* (2013.01); *B21B 1/463* (2013.01); *B22D 11/0631* (2013.01); *C21D 3/04* (2013.01); *C21D 8/0226* (2013.01); *C21D 8/0236* (2013.01); *C22C 38/02* (2013.01); *C22C 38/06* (2013.01); *C22C 38/38* (2013.01); *G01N 3/08* (2013.01); *B21B 2265/14* (2013.01); *C21D 2211/001* (2013.01); *C21D 2211/005* (2013.01)

(58) Field of Classification Search
CPC ...... C21D 9/52; C21D 8/0226; C21D 8/0236; C21D 3/04; C22C 38/38
See application file for complete search history.

(56) References Cited

U.S. PATENT DOCUMENTS

| | | |
|---|---|---|
| 3,201,230 A | 8/1965 | Mitchell |
| 4,866,662 A | 9/1989 | Zimmer |
| 2012/0121452 A1 | 5/2012 | Spitzer et al. |
| 2013/0240520 A1 | 9/2013 | Braun et al. |
| 2014/0367066 A1 | 12/2014 | Evertz et al. |
| 2015/0013845 A1 | 1/2015 | Georgeou |

FOREIGN PATENT DOCUMENTS

| | | |
|---|---|---|
| DE | 199 00 199 A1 | 7/2000 |
| DE | 10 2004 061 284 A1 | 7/2005 |
| DE | 10 2005 052 774 A1 | 6/2006 |
| EP | 0 489 727 B1 | 8/1995 |
| EP | 0 573 641 B1 | 9/1998 |
| WO | WO 2006/048034 A1 | 5/2006 |
| WO | WO 2010/102596 A1 | 9/2010 |

OTHER PUBLICATIONS

English International Search Report issued by the European Patent Office in International Application PCT/DE2015/100147.

*Primary Examiner* — Jessee R Roe
(74) *Attorney, Agent, or Firm* — Henry M. Feiereisen LLC

(57) ABSTRACT

A method is disclosed for calculating the combination of properties of phase components and of mechanical properties being established of a predefined alloy composition for a deformable lightweight steel having the elements in percent by weight C 0.02 to ≤1.0, Al 2.5 to ≤8.0, Si 0.0 to ≤1.5, Mn ≥5.0 to ≤35.0, Cr >1.0 to ≤14.0, total content of N, S, P ≤0.1, the remainder iron and other steel-accompanying elements with some contents of Cu, Mo, Ni, and Zn of up to 1.0 wt % in total by using specific formulas on the basis of the manganese content, wherein, in the formulas, the alloy contents are used as absolute numbers without dimensions, and the calculated, dimensionless values are assigned the units MPa for Rm and Rp and % for A80.

15 Claims, 1 Drawing Sheet

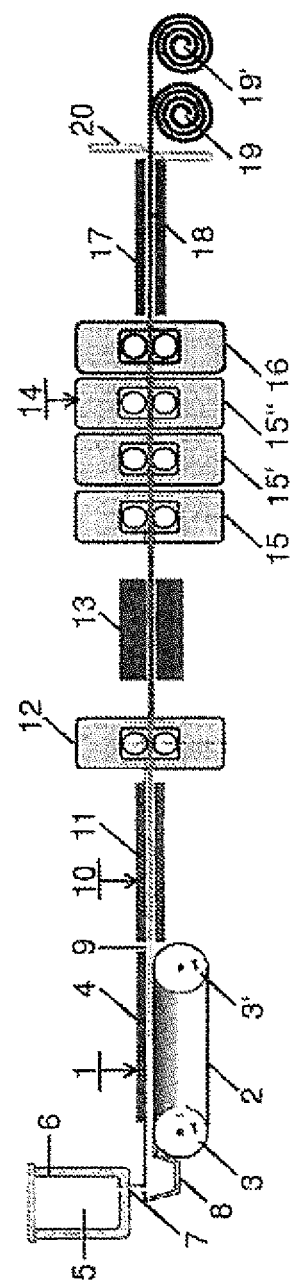

METHOD FOR CALCULATING THE COMBINATION OF PROPERTIES BEING ESTABLISHED FOR A DEFORMABLE LIGHTWEIGHT STEEL

CROSS-REFERENCES TO RELATED APPLICATIONS

This application is the U.S. National Stage of International Application No. PCT/DE2015/100147, filed Apr. 8, 2015, which designated the United States and has been published as International Publication No. WO 2015/158328 and which claims the priority of German Patent Application, Serial No. 10 2014 005 662.7, filed Apr. 17, 2014, pursuant to 35 U.S.C. 119(a)-(d).

BACKGROUND OF THE INVENTION

The invention relates to a method for calculating the resulting property combination of phase proportions and mechanical properties of a given alloy composition for a formable lightweight steel according to the preamble of patent claim 1.

Especially the hotly contested automobile market forces manufacturers to constantly seek solutions for lowering the fleet consumption while maintaining a highest possible comfort and passenger protection. Hereby on one hand the weight saving of a all vehicle components plays important role but also properties of the individual components that increase the passive safety of the passengers at high static and dynamic stress during operation and in the event of a crash.

In recent years significant advances have been made in the field of so-called lightweight steels, which are characterized by a low specific weight and at the same time high strengths and tenacity (for example EP 0 489 727 B1, EP 0 573 641 B1, DE 199 00199 A1) and a high ductility and are therefore of great interest for vehicle construction.

In these steels, which are austenitic in the starting state, the high proportion of alloy components with a specific weight far below the specific weight of iron (Mn, Si, Al) achieves a weight reduction, which is advantageous for the automobile industry while being able to maintain a conventional design.

From DE 10 2004 061 284 A1 for example a lightweight steel is known with an alloy composition (in weight %):

| | | |
|---|---|---|
| C | 0.04 to | ≤1.0 |
| Al | 0.05 to | ≤4.0 |
| Si | 0.05 to | ≤6.0 |
| Mn | 9.0 to | <18.0 | remainder iron, inducing usual steel-accompanying elements. Optionally depending on the demand, Cr, Cu, Ti, Zr, V and Nb can be added.

This known lightweight steel has a partially stabilized γ solid solution microstructure with a defined stacking fault energy with a partially multiple TRIP-effect which transforms the tension- or expansion-induced transformation of a face-centered γ solid solution (austenite) into an ε-martensite (hexagonally densest spherical packing) and upon further deformation into a body-centered α martensite and residual austenite.

The high degree of deformation is achieved by TRIP— (Transformation Induced Plasticity) and TWIP—(Twinning Induced Plasticity) properties of the steel.

Many tests have revealed that in the complex interaction between Al, Si and Mn the carbon content is of paramount importance. Carbon on one hand increases the stacking fault energy and on the other hand widens the metastable austenite region. As a result the deformation-induced martensite formation and the strengthening associated therewith and also the ductility can be influenced.

It is also known that Mn and c are relatively strong austenite formers in contrast to Al Cr and Si, which are ferrite formers. A combination of these elements therefore leads to the formation of the two main phases austenite and ferrite and to further phases such as ordered ferrite phases and/or carbon based precipitations. These also play an important role for the mechanical technological properties of these steels.

Beside the influence on the formation of the microstructure phases an increasing proportion of Al and Si allows to further reduce the density of the steel/a problem however is that with increasing contents of Al or Si the casting with the known methods by macro segregations or bending of the strip or band during the solidification is more difficult or even impossible. Steel with Al— contents of >2% forms an oxide ($Al_2O_3$) during solidification at air which is extremely hard and brittle and thus makes casting and further processing difficult or even impossible. Thus process technical limits complicate the production of lightweight steels with ever-lower density significantly below the normal density of about 7.85 gr/cm$^3$.

In addition the tests have revealed that lightweight steels are often already at small variations of the phase proportions of austenite and ferrite display great differences regarding strength at otherwise constant elongation and great differences regarding elongation at almost constant strength. Depending on the alloy composition, i.e., the interaction between austenite and ferrite formers, the phase proportions can hereby+ for example be between 5 and almost 100%, with strengths Rm between 600 and 1200 MPa, yield strengths Rp0.2 of 300 to 1120 MPa and elongation A80 between 5 and 40%.

The tests have also shown that different alloy compositions can lead to the same phase proportions of austenite and ferrite but nevertheless have very different mechanical properties. On the other hand lightweight steels with comparable mechanical properties may have very different phase proportions of austenite and ferrite.

However, due to the complex interactions between the individual alloy components it is still very difficult if not impossible to predict phase proportions and/or mechanical properties of these steels, so that materials with the demanded properties can only be determined by performing laborious and expensive tests.

SUMMARY OF THE INVENTION

It is therefore an object of the invention to provide a method for calculating the resulting property combinations of phase proportions and mechanical properties of a given alloy composition for a formable lightweight steel with which the mechanical properties can be predicted in good approximation by using different austenite/ferrite phase proportions of the steel.

A further object is to provide a method for further processing of such a calculated and subsequently produced lightweight steel to a hot strip with which also lightweight steels with increased Al contents of 2.5 weight % can be reliably produced.

The object relating to the method for calculating the resulting property combinations is solved based on the preamble in connection with the characterizing features of the corresponding independent method claim for calculating. Advantageous embodiments are the subject matter of dependent claims. A method according to the invention for further processing such a calculated lightweight steel into a steel strip is set forth in the corresponding independent method claim.

According to the teaching of the Invention the object is solved by a method for a formable lightweight steel with the elements in weight %:

| | | |
|---|---|---|
| C | 0.02 to | ≤1.0 |
| Al | 2.5 to | ≤8.0 |
| Si | 0.0 to | ≤1.5 |
| Mn | 5.0 to | ≤35.0 |
| Cr | >1.0 to | ≤14.0 | with N, S, P in sum together ≤0.1, remainder iron and other steel accompanying elements with possible contents of Cu, Mo, Ni and Zn in sum together up to 1.0 weight %, wherein the lightweight steel consists of a phase mixture of austenite and ferrite (A/F) with an austenite proportion between 100% and 5%, a strength Rm between 600 and 1200 MPa, a yield strength Rp0.2 between 300 and 1120 MPa and a elongation at break A80 between 5 and 40% according to the following formulas in dependence on the manganese content, wherein absolute numbers without dimension are inserted into the following formulas and the units MPa for Rm and Rp and % for A80 are assigned to the dimensionless values.

For Mn-contents of 5 up to at most 11% the following formulas apply:

$$Rm = 3182\{C\} + 1224\{Si\} + 847.6\{Cr\} + 633.2\{Al\} - 3354.8 - 140.7\{Al\}\{Cr\} - 482.5\{Cr\}\{C\} - 1372.3\{Si\}^2$$

$$Rp = 2509.2\{C\} + 947\{Si\} + 538\{C\} + 367.8\{Al\} - 2168.1 - 78.1\{Al\}\{Cr\} - 381.9\{Cr\}\{C\} - 923.2\{Si\}^2$$

$$A80 = 267.4 + 48\{Al\}\{C\} - 2.6\{Cr\} - 16.8\{Si\} - 41.1\{Al\} - 275.4\{C\}$$

wherein the following content limits in weight % are to be observed:
C: 0.2 to 0.7
Si≤1.0
Al+Cr≤12

For Mn contents of more than 11 up to at most 22% the following formulas apply:

$$Rm = 322.7\{C\} + 103\{Si\} + 847.6\{Cr\} + 55\{Al\} + 195.8\{Cr\}\{C\} - 15\{C\}\{Cr\}^2$$

$$Rp = 132\{Si\}101.8\{Cr\} + 60.6\{Al\} + 91\{Cr\}\{C\} - 11.9\{Cr\}^2$$

$$A80 = 24 + 46.5\{Si\} + 48\{C\}^2 - 7.9\{Cr\}\{C\} - 8.8\{Al\}\{Si\}$$

wherein the following content limits in weight % are to be observed:
C: <0.6
Si: >0.4 to 1.2
Al: 1 to 9
Cr: ≤10

For Mn contents of more than 22 up to at most 35% the following formulas apply:

$$Rm = 104.3\{Cr\} + 2766.6\{Si\}^2 + 11.7\{Al\}2 - 172.8\{Cr\}\{Si\} - 282.3\{Al\}\{Si\}^2$$

$$Rp = 3269\{Si\} + 234.2\{Cr\}335.6\{Al\}\{C\} - 1266.5 - 188.4\{Al\}\{Si\} - 1391.6\{Cr\}\{Si\}\{C\}$$

$$A80 = 33.5 + 88.7\{Si\}\{C\} - 2.1\{Cr\} - 4.5\{Al\}\{C\} - 36\{Si\}^2$$

wherein the following content limits in weight % are to be observed:
C: 0.2 to 0.7
Si: 0.3 to 1.5
Al+Cr≤12

This new method utilizes the circumstance that laws exist that describe the mechanical properties of the steel in dependence on the present alloy composition wherein different proportions of the microstructure phases in particular the resulting proportions of austenite and ferrite hereby play a role.

Based on extensive tests on lightweight alloys the phase proportions of austenite and ferrite and the respective mechanical properties such as tensile strength, yield strength and elongation at break were determined and regression calculations were performed with which now the properties of a steel can be determined based on a defined alloy.

The results of the following examples show that the results of the regression calculations match with the results of the mechanical tests on the tested alloys in very good approximation. The values in brackets are the values calculated according to the invention

| Alloy | Rm (MPa) | Rp0.2 (MPa) | A80 (%) |
|---|---|---|---|
| L1:5Mn—6Al—4Cr—1Si—0.6C | 1077 (1047) | 918 (918) | 5 (4) |
| L2:12Mn—6Al—6Cr—0.6Si—0.4C | 964 (968) | 842 (844) | 8 (9) |
| L3:22Mn—4Al—6Cr—0.5Si—0.4C | 815 (848) | 696 (709) | 19 (18) |
| L4:33Mn—9AL—2Cr—1.25Si—0.6C | 1052 (1077) | 817 (893) | 18 (15) |

Based on the regression calculations clear dependencies of the mechanical properties on the alloy composition at hand can thus be determined.

Depending on the alloy composition at hand the mechanical properties of the steel can thus advantageously be determined without requiring expensive production and subsequent testing for determining these characteristic values.

For a steel 15Mn-6Al-6Cr-0.6Si-0.4C a strength Rm of 968 MPa results, a yield strength Rp of 844 MPa and a A80 value of 9% at a phase content of 80% austenite.

The steel 10Mn6Al-6Cr-0.3Si-0.3C according to the inventive concept has a strength Rm of 795 MPa, a yield strength Rp of 721 MPa and a A80 value of 4% at a phase content of 42%.

The method according to the invention thus allows determining in a simple, cost-effective and reliable manner the resulting property combinations of phase proportions and mechanical properties of a given alloy composition for a formable lightweight steel without having to perform laborious and expensive tests on materials with different alloy compositions.

For producing hot strips cost-effectively and with consistent quality from alloys with increased aluminum contents of 2.5% and above, a method for further processing a lightweight steel produced according to claims 1 to 4 with predetermined alloy composition is used according to the invention in which the melt is cast in a horizontal casting system under calm flow and in the absence of bending into a pre-strip with a thickness in the range between 6 and 30 mm and is subsequently rolled into a hot strip with a degree of deformation of at least 50% at thicknesses from 0.9 to 6.0 mm. Prior to the hot rolling an annealing process at 800 to 1200° C. may be required.

The advantage of the proposed method is that when using a horizontal strip casting system macro-segregations and blowholes can be avoided to the most part due to very homogenous cooling conditions in the horizontal casting system. Because in these systems no casting powder is used the problems relating to casting powder are not present.

In order to accomplish the calm flow in the strip casting process it is proposed to use an electromagnetic brake, which generates a field and runs synchronously or with the strip or with an optimal speed relative to the strip, which ensures that in the ideal case the speed of the melt supply equals the speed of the rotating conveyor belt. The bending, which is regarded as disadvantageous during the solidification, is avoided in that the bottom side of the belt that receives the melt is supported on a plurality of adjacent rollers. The support is enhanced by generating a negative pressure in the region of the casting belt so that the casting strip is strongly pressed onto the rollers. In addition the Al-rich or Si-rich melt solidifies in an almost oxygen-free furnace atmosphere. In conventional routes above 1250° C. the Si-rich scale (Fayalit) liquefies and is extremely difficult to remove. This can be avoided by a corresponding temperature-time-course in the housing and by the following process steps.

In order to maintain these conditions during the critical phase of the solidification, the length of the conveyor belt is selected so that at the end of the conveyor belt the strip is fully solidified to the most part prior to deflection of the conveyor belt.

Adjoining the end of the conveyor belt is a homogenization zone, which is used for a temperature compensation and possible tension reduction.

The pre-strip can be rolled into the hot strip either in-line or separately off-line. After being produced and prior to the off-line rolling the pre-strip can either be directly coiled in a hot state or can be cut into plates prior to the cooling. After an optional cooling the strip or plate material is then reheated and uncoiled for the off-line rolling or is reheated as plate.

BRIEF DESCRIPTION OF THE DRAWING

The sole FIGURE shown in the appendix schematically shows a method sequence according to the Invention for the condition casting speed=rolling speed.

Prior to the hot rolling process the casting method is performed with a horizontal strip casting system 1, consisting of a rotating conveyor belt 2 and two deflection rolls 3, 3'. Also a lateral sealing 4 can be seen which prevents the applied melt 5 from flowing off the conveyor belt 2 to the right and left. The melt 5 is transported to the strip casting system 1 by means of a ladle 6 and flows through an opening 7 arranged on the bottom into a supply container 8, which is constructed as an overflow container.

DETAILED DESCRIPTION OF PREFERRED EMBODIMENTS

Not shown are the devices for intensive cooling of the bottom side of the upper scaffold of the conveyor belt 2 and the complete housing of the strip casting system 1 with corresponding protective gas atmosphere.

After application of the melt 5 onto the rotating conveyor belt 2 the intensive cooling leads to solidification and formation of a pre-strip 9, which at the end of the conveyor belt 2 is fully solidified to the most part.

For temperature compensation and tension reduction a homogenization zone 10 adjoins the strip casting system 1. The homogenization zone consists of a heat-insulated housing 21 and a here not shown roller table.

The scaffold 12 following thereafter is either configured only as a pure driver aggregate optionally with a small reduction, or as a rolling aggregate with a predetermined reduction.

Following is an intermediate heating, advantageously here configured as an inductive heating for example in the form of a coil 13. The actual hot forming takes places in the following scaffold series 14, wherein the first three scaffolds 15, 15' 15" cause the actual thickness reduction, while the last scaffold 16 is configured as smoothing rolls.

After the last pass a cooling zone 17 follows in which the finished hot strip is cooled down to coiling temperature.

Between the end of the cooling zone 17 and the coil 19, 19' a cutter 20 is arranged. The cutter 20 has the purposed to divide the hot strip 18 transversely as soon as one of the two coils 19, 19' is completely wound up. The beginning of the following hot strip 18 is then conducted to the second freed coil 19, 19', this ensures that the strip tension is maintained over the entire strip length. This is particularly important for generating thin hot strips.

Not shown in the FIGURE are the system components for reheating the pre-strip 9 prior to the hot rolling and for cold rolling the hot strip.

The invention claimed is:

1. A method for producing a formable lightweight steel with the elements in weight %

| | |
|---|---|
| C | 0.02 to ≤ 1.0 |
| Al | 1 to 9 |
| Si | 0.0 to ≤ 1.5 |
| Mn | 6.0 to ≤ 35.0 |
| Cr | >1.0 to ≤ 14.0 |

With N, S, P in sum together ≤0.1, remainder iron and other steel accompanying elements, and optionally Cu, Mo, Ni and Zn in sum together up to 1.0 weight %, wherein the lightweight steel is made of a phase mixture of austenite and ferrite (A/F) with an austenite proportion between 100% and 5%, a strength Rm between 600 and 1200 MPa, a yield strength Rp0.2 between 300 and 1120 MPa, and a elongation at break A80 between 5 and 40% said method comprising:

for a first given alloy composition of said formable lightweight steel in which Mn: 5 to maximal 11%, calculating a strength Rm and Rp in MPa and an elongation at break A80 in % of the formable lightweight steel according to the formulas:

$$Rm=3182\{C\}+1224\{Si\}+847.6\{Cr\}+633.2\{Al\}-3354.8-140.7\{Al\}\{Cr\}-482.5\{Cr\}\{C\}-1372.3\{Si\}^2$$

$$Rp=2509.2\{C\}+947\{Si\}+538\{C\}+367.8\{Al\}-2168.1-78.1\{Al\}\{Cr\}-381.9\{Cr\}\{C\}-923.2\{Si\}^2$$

$$A80=267.4+48\{Al\}\{C\}-2.6\{Cr\}-16.8\{Si\}-41.1\{Al\}-275.4\{C\}$$

Wherein the following content limits are to be observed:
C: 0.2 to 0.7, Si: ≤1.0%, and a sum of Al+Cr: ≤12%;

for a second given composition of said formable lightweight steel in which 22%≥Mn>11%, calculating the strength Rm and Rp in MPa and the elongation at break A80 in % of the formable lightweight steel according to the formulas:

$$Rm=322.7\{C\}+103\{Si\}+847.6\{Cr\}+55\{Al\}+195.8\{Cr\}\{C\}-15\{C\}\{Cr\}^2$$

$$Rp=132\{Si\}101.8\{Cr\}+60.6\{Al\}+91\{Cr\}\{C\}-11.9\{Cr\}^2$$

$$A80=24+46.5\{Si\}+48\{C\}^2-7.9\{Cr\}\{C\}-8.8\{Al\}\{Si\},$$

wherein the following content limits are to be observed: C <0.6%, Si >0.4 to 1.2, Al: 1 to <9% and Cr: ≤10%;
for a third given composition of said formable lightweight steel in which Mn: >22% to 35%, calculating the strength Rm and Rp in MPa and the elongation at break A80 in % of the formable lightweight steel according to the formulas:

$$Rm=104.3\{Cr\}+2766.6\{Si\}^2+11.7\{Al\}2-172.8\{Cr\}\{Si\}-282.3\{Al\}\{Si\}^2$$

$$Rp=3269\{Si\}+234.2\{Cr\}335.6\{Al\}\{C\}-1266.5-188.4\{Al\}\{Si\}-1391.6\{Cr\}\{Si\}\{C\}$$

$$A80=33.5+88.7\{Si\}\{C\}-2.1\{Cr\}-4.5\{Al\}\{C\}-36\{Si\}^2$$

wherein the following content limits are to observed: C: 0.2 to 0.7%, Si: 0.3 to 1.5%, and a sum of Al+Cr: ≥12%,
wherein absolute numbers without dimension are inserted into the formulas and the unit MPa for Rm and Rp and % for A80 are assigned to the dimensionless values; and producing a hot strip with any of the first, second and third given composition by casting a melt in a horizontal strip casting system in the absence of bending into a pre-strip with a thickness in the range between 6 and 30 mm, and rolling the pre-strip into a hot strip with a degree of deformation of at least 50%.

2. The method of claim 1, wherein a speed of a supply of the melt is equal to the speed of the rotating conveyor belt.

3. The method of claim 1, wherein approximately same cooling conditions result for all surface elements of a strip shell of the strip that forming at a beginning of solidification of the strip and extending over a width of the conveyor belt.

4. The method of claim 1, wherein the melt applied onto the conveyor belt is fully solidified to the most part at the end of the conveyor belt.

5. The method of claim 4, further comprising after full solidification and prior to a further processing, passing the pre-strip through a homogenization zone.

6. The method of claim 5, wherein the further processing comprises cutting the pre-strip into plates.

7. The method of claim 6, further comprising after the cutting of the pre-strip into plates, heating the plates to a rolling temperature and are then subjected the plates to the rolling process.

8. The method of claim 5, wherein the further processing comprises coiling the pre-strip.

9. The method of claim 8, further comprising after the coiling up the pre-strip is coiling the pre-strip, heating the pre-strip to rolling temperature and subjecting the pre-strip to the rolling process.

10. The method according of claim 8, further comprising preheating the pre-strip prior to the uncoiling.

11. The method of claim 1, wherein the pre-strip is subjected to the rolling process in-line and is then wound up.

12. The method of claim 1, wherein the degree of deformation during the hot rolling is >70%.

13. The method of claim 1, wherein the degree of deformation during the hot rolling is >90%.

14. The method of claim 1, wherein the hot strip is reheated and is cold rolled after the cooling.

15. The method of claim 1, further comprising an annealing process performed in a decarburizing atmosphere.

* * * * *

UNITED STATES PATENT AND TRADEMARK OFFICE
CERTIFICATE OF CORRECTION

PATENT NO. : 10,435,764 B2  
APPLICATION NO. : 15/304743  
DATED : October 8, 2019  
INVENTOR(S) : Zacharias Georgeou and Frank Klose Page 1 of 1

It is certified that error appears in the above-identified patent and that said Letters Patent is hereby corrected as shown below:

On the Title Page

Item [56] References Cited  
US PATENT DOCUMENTS: Replace "US 4,866,662" with the correct -- US 4,865,662 --.

In the Claims

In Column 7, Claim 1, Line 14: Replace "1 to < 9%" with -- 1 to ≤ 9% --.

In Column 7, Claim 1, Line 20: Replace "11.7{Al}2" with -- $11.7\{Al\}^2$ --.

In Column 7, Claim 1, Line 30: Replace "> 12%" with -- ≤ 12% --.

Signed and Sealed this  
Seventh Day of July, 2020

Andrei Iancu  
*Director of the United States Patent and Trademark Office*